United States Patent
Klinger et al.

(10) Patent No.: US 6,187,956 B1
(45) Date of Patent: Feb. 13, 2001

(54) METHOD FOR PREPARING OF L-PHENYLEPHRINE HYDROCHLORIDE

(75) Inventors: Franz Dietrich Klinger, Griesheim; Lienhard Wolter, Hochstetten/Dhaun; Wolfgang Dietrich, Bad Kreuznach, all of (DE)

(73) Assignee: Boehringer Ingelheim Pharma KG, Ingelheim (DE)

( * ) Notice: Under 35 U.S.C. 154(b), the term of this patent shall be extended for 0 days.

(21) Appl. No.: 09/487,050

(22) Filed: Jan. 19, 2000

(30) Foreign Application Priority Data

Jan. 21, 1999 (DE) ............................................... 199 02 229

(51) Int. Cl.⁷ ................................................. C07C 209/00
(52) U.S. Cl. ............................................................ 564/358
(58) Field of Search ............................................. 564/358

(56) References Cited

U.S. PATENT DOCUMENTS 5,767,276   6/1998   Zhang .

FOREIGN PATENT DOCUMENTS 14 23 911   2/1976   (GB) .

OTHER PUBLICATIONS

Hayashi, Katsumura, Konishi and Kumada; "Asymmetric Synthesis of 2–Amino–1–Arylethanols by Catalytic Asymmetric Hydrogenation"; Tetrahedron Letters No. 5, pp. 425–428;; Great Britain (1997).

Takeda, Tachinami and Aburatani; "Practical Asymmetric Synthesis of (R)–(–)–Phenylephrine Hydrochloride Catalyzed by (2R, 4R),–MCCPM–Rodium Complex 1,2"; Tetrahedron Letters, vol. 30, No. 3, pp. 367–370, 1989; Great Britain.

Sakuraka, Takahashi, Takeda and Achiwa; "Efficient Asymmetric Hydrogenation of x–Amino Ketone Derivatives. A Highly Enantioselective Synthesis of Phenylephrine, Levamisole, Carnitine and Propranolol 1"; Chem. Pharm. Bull. 43(5) pp. 738–747; 1995.

*Primary Examiner*—Samuel Barts
(74) *Attorney, Agent, or Firm*—Robert P. Raymond; Timothy X. Witkowski; Mary-Ellen Devlin

(57) ABSTRACT

The present invention relates to an improved process for preparing L-phenylephrine hydrochloride 3 on an industrial scale by asymmetric hydrogenation as the key step and a special sequence of subsequent steps, using [Rh(COD)Cl]₂ as catalyst and a chiral, two-pronged phosphine ligand such as (2R,4R)-4-(dicyclohexylphosphino)-2-(diphenylphosphino-methyl)-N-methyl-aminocarbonyl-pyrrolidine as the catalyst system.

22 Claims, No Drawings

METHOD FOR PREPARING OF L-PHENYLEPHRINE HYDROCHLORIDE

FIELD OF THE INVENTION

The present invention relates to an improved process for preparing L-phenylephrine hydrochloride by means of rhodium-catalysed asymmetric hydrogenation on an industrial scale.

TECHNOLOGICAL BACKGROUND TO THE INVENTION

L-phenylephrine is one of the analogues of adrenaline frequently used for pharmaceutical purposes and is of great commercial interest. L-phenylephrine is used pharmaceutically in the form of L-phenylephrine hydrochloride and acts as a sympathomimetic in the treatment of hypotonia and as a vasoconstrictor in ophthalmology and rhinology. The chemical structure of the chiral α-aminoalcohol L-phenylephrine is shown in formula I.
Formula I:

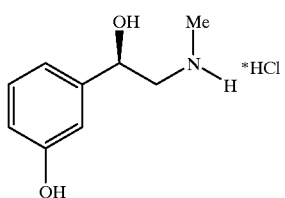

PRIOR ART

The methods of preparing L-phenylephrine hydrochloride known from the prior art include the asymmetric hydrogenation of the prochiral N-benzyl-N-methyl-2-amino-m-benzyloxyacetophenone hydrochloride (formula II) according to Tetrahedron Letters 30 (1989), 367–370, or Chem. Pharm. Bull. 43 (5) (1995) 738–747.
Formula II:

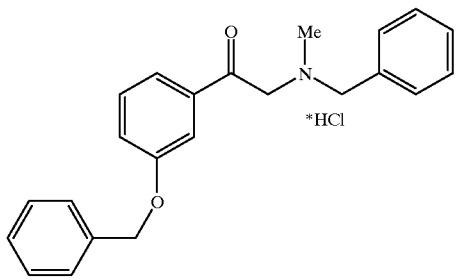

Achiwa et al. writing in Tetrahedron Letters 30 (1989), 367–370 describe the asymmetric hydrogenation of 3-benzyloxy-2-(N-benzyl-N-methyl)-aminoacetophenone hydrochloride as a substrate with hydrogen in the presence of [Rh(COD)Cl]$_2$/(2R,4R)-4-(dicyclohexylphosphino)-2-(diphenylphosphino-methyl)-N-methyl-aminopyrrolidine as catalyst. Immediately after filtration and concentration of the reaction mixture the benzylic nitrogen protecting group is cleaved and phenylephrine is obtained as the product. In addition to the L-enantiomer, the D-enantiomer is obtained in a proportion of at least 7.5% as an impurity (85% ee). For the reaction, the catalyst has to be used in a molar ratio of 1:2000 based on the substrate. The main disadvantage of the process is that the L-phenylephrine obtained cannot be purified economically to a degree of purity of at least 98% ee which is essential if it is to be used as a pharmaceutical composition.

In Chem. Pharm. Bull. 43 (5) (1995) 738–747 a molar ratio of substrate to catalyst of about 1,000:1 is given as the preferred ratio for asymmetric hydrogenation.

However, the process described in the prior art is unsuitable for the production of L-phenylephrine on an industrial scale on account of a number of disadvantages: In spite of the use of large amounts of catalyst in the asymmetric reaction step the product cannot be prepared as the L-enantiomer with sufficient purity for pharmaceutical purposes without expensive purification procedures, but is only obtainable as a mixture containing a relatively large amount of D-enantiomer as a contaminant.

In addition, the relatively long reaction time of the step of asymmetric hydrogenation of about 20 hours constitutes a very equipment-intensive and expensive reaction step precisely for the production of L-phenylephrine on an industrial scale, with a by no means negligible safety risk.

DESCRIPTION OF THE INVENTION

The present invention relates to a new method of producing L-phenylephrine hydrochloride by asymmetric hydrogenation which overcomes the difficulties and drawbacks known from the prior art or mentioned above.

One of the essential goals of the present invention is to develop a process by means of which L-phenylephrine hydrochloride can be prepared with high optical and chemical purity. At the same time, the risk of contamination of drug preparations containing L-phenylephrine hydrochloride as active substance with the unwanted D-enantiomer should be minimised.

Another objective of the invention is to develop a process by means of which largely enantiomerically pure L-phenylephrine can easily be prepared.

A further goal of the invention is to prepare L-phenylephrine by a stereoselective process in order to avoid reaction steps in which chiral intermediate compounds or the chiral end product L-phenylephrine is obtained as a racemate in a similar amount to the corresponding antipode.

The process according to the invention further sets out to shorten significantly the hydrogenation times required for the preparation of L-phenylephrine hydrochloride, in order to reduce the costs and dangers involved in the use of hydrogen under high pressure, inter alia.

Another aim of the present invention is to provide the skilled person with a process for preparing L-phenylephrine by which this active substance which is needed in large quantities is cheaply obtainable starting from readily available educts.

Surprisingly, it has now been found that L-phenylephrine hydrochloride can be obtained with exceptionally high optical purity from N-benzyl-N-methyl-2-amino-m-hydroxyacetophenone hydrochloride 1 by asymmetric hydrogenation with [Rh(COD)Cl]$_2$/(2R,4R)-4-dicyclohexylphosphino)-2-(diphenylphosphino-methyl)-N-methyl-aminocarbonylpyrrolidine as the catalyst system and a special sequence of steps. The abbreviation COD used in the overall formula stands for cyclooctadiene.

With a molar ratio of catalyst to substrate of about 1:1000, starting from benzyladrianone (N-benzyl-N-methyl-2-amino-m-hydroxy-acetophenone-hydrochloride) 1, benzyladrianol hydrochloride 2 is obtained by the process according to the invention with an optical purity of 92% ee (reaction plan 1). By converting the benzyladrianol hydrochloride 2 into the free base and then precipitating it from an ammonia/methanol/water mixture, the optical purity can easily and remarkably be improved even to >99% ee. This intermediate compound which is sufficiently pure for pharmaceutical purposes is then converted into L-phenylephrine hydrochloride 3 in a subsequent reaction step.

The precise mechanism of the rhodium-catalysed asymmetric hydrogenation is not presently known. This is particularly true of the reaction of N-benzyl-N-methyl-2-amino-m-hydroxyacetophenone hydrochloride 1 with hydrogen catalysed by [Rh(COD)Cl]$_2$ and (2R,4R)-4-(dicyclohexylphosphino)-2-(diphenylphosphino-methyl)-N-methyl-aminocarbonylpyrrolidine as the catalyst system. Reaction plan 1:

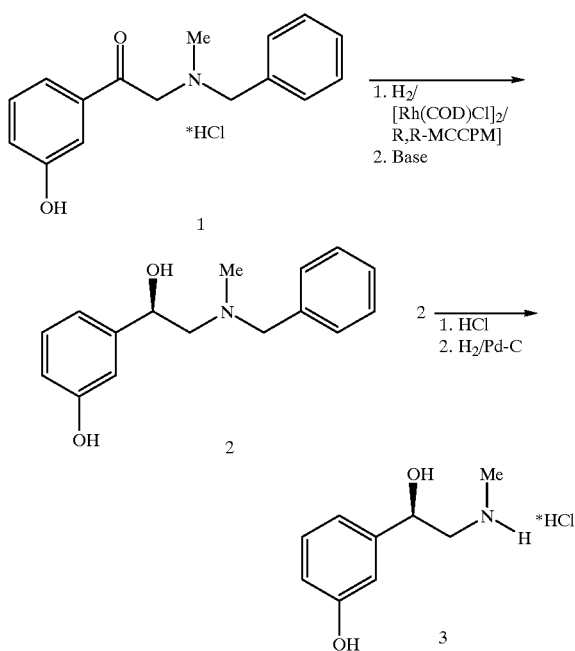

It has also been found that, contrary to the prevailing opinion, a molar ratio of catalyst to substrate of about 1:1000 is not necessary for the asymmetric hydrogenation step in order to achieve good yields or high optical purity, as indicated by the prior art. In the process according to the invention, this ratio can be dramatically lowered by a factor of 10 to 100. In spite of this significant reduction in the amount of catalyst the intermediate product 2 resulting from the asymmetric hydrogenation—and hence eventually L-phenylephrine—is still obtained with a significantly higher optical yield than in the process known from the prior art. Thus, for example, L-phenylephrine is still obtained in an optical yield of 88% ee with a catalyst concentration of only 1:10,000. Reducing the amount of catalyst makes the purification of the product considerably easier.

By reducing the amount of catalyst and using the commercially favourable N-benzyl-N-methyl-2-amino-m-hydroxyacetophenone 1 as educt, the costs of preparing L-phenylephrine can be reduced substantially by the new process.

In addition, the new process reduces the reaction time for asymmetric hydrogenation by up to 75% compared with the prior art. It is particularly advantageous for the production of L-phenylephrine on an industrial scale precisely from the point of view of costs and safety.

Finally, with the process according to the invention, it is possible to omit the protection of the phenolic hydroxy group in the 2-aminoketone 1 and still successfully react 1 to form the chiral 2-aminoalcohol 2 by asymmetric hydrogenation with one of the catalyst systems according to the invention.

Moreover, by purification at the benzyladrianol stage 2 the process according to the invention makes it possible to obtain L-phenylephrine with high optical purity.

According to reaction plan 1 the commercially favourable N-benzyl-N-methyl-2-amino-m-hydroxyacetophenone 1 is reacted with hydrogen in a first reaction step in the presence of a chiral rhodium catalyst under a pressure in the range from 10 to 100 bar, preferably 10 to 50 bar and most preferably at 20 bar, to obtain N-benzyl-L-phenylephrine hydrochloride 2.

According to the invention [Rh(COD)Cl]$_2$ and a chiral, bidentate phosphine ligand is used as catalyst. Preferably, (2R,4R)-4-(dicyclohexylphosphino)-2-(diphenylphosphino-methyl)-N-methyl-aminocarbonylpyrrolid (RR-MCCPM) is used as catalyst. The preparation of this catalyst is known from the prior art [EP-A-0 251 164, EP-A-0 336 123]. The catalyst may also be polymer-bound, e.g. the chiral ligand (2R,4R)-4-dicyclohexylphosphino)-2-(diphenylphosphino-methyl)-N-methyl-aminocarbonyl)pyrrolidine is bound to a polymer via the phenyl groups, for example. The use of such polymer-bound ligands does not absolutely rule out the simultaneous use of non-polymer-bound ligands. Polymer-bound catalysts of this kind are particularly advantageous for simple purification of the product.

The catalyst is either put in as a pre-prepared, oxygen-free solution of [Rh(COD)Cl]$_2$ and ligand or prepared in situ from [Rh(COD)Cl]$_2$ and ligand in the presence of N-benzyl-N-methyl- 2-amino-m-hydroxyacetophenone hydrochloride 1, without oxygen, under a protective gas atmosphere or a hydrogen atmosphere.

The molar ratio of N-benzyl-N-methyl-2-amino-m-hydroxyacetophenone hydrochloride 1 and catalyst is between 5,000:1 and 100,000:1, preferably between 5,000:1 and 20,000:1 and most preferably about 10,000:1 in the process according to the invention.

The hydrogenation is carried out at a reaction temperature of about 40 to 100° C. The preferred temperature range is between 40 and 60° C.; temperatures in the range from 50–55° C. are most preferred.

The reaction media used may be either protic solvents such as alcohols and/or water, or aprotic polar solvents such as ethers and/or amides or lactams and/or mixtures thereof. Water may be added to all the solvents if required. Preferably, branched or unbranched $C_1$–$C_8$ alkanols are used as protic solvents. Most preferably, lower alcohols such as methanol, ethanol, n-propanol and isopropanol or mixtures thereof may be used. Methanol is particularly preferred as the reaction medium, and the methanol or the other alcohols or solvents may optionally contain water. Suitable aprotic solvents are polar ethers such as, for example, tetrahydrofuran or dimethoxyethylethers or amides such as dimethylformamide, or lactams such as N-methylpyrrolidone, for example. Solvents with low flammability are preferably used.

Since the educt 1 occurs as the hydrochloride, it is first converted into the free base by the addition of a base in situ, in order to increase the solubility. The bases used may be organic or inorganic bases, both as solids and in the form of solutions, e.g. aqueous solutions. Suitable inorganic bases are basically reacting alkali metal salts or alkali metal hydroxides. Preferably, alkali metal hydrogen carbonates or alkali metal carbonates are used in addition to alkali metal hydroxides. It is particularly preferable to use $Na_2CO_3$, $K_2CO_3$, LiOH, NaOH, KOH or $NaHCO_3$. The invention also includes the use of other substances reacting in a basic manner or other substances which are capable of converting the hydrochloride 1 into the free base and are known from the prior art. Suitable organic bases are, in particular, tert. alkyl-amines or tert. alkyl-aryl-amines. Preferably, trialkylamines with branched or unbranched $C_1$–$C_5$-alkyl groups are used. Triethylamine and diisopropylethylamine have proved particularly suitable, for example. If desired, the reaction may also be carried out in the presence of basic polymers with for example tert. amino functions.

The asymmetric hydrogenation is carried out at a pressure of between more than 1 bar and a maximum of 100 bar, preferably between 10 and 50 bar, and most preferably at about 20 bar.

The reaction is carried out with the exclusion of oxygen, expediently under inert gas, preferably in a hydrogen atmosphere. However, it is not essential for the reaction that the hydrogen for the hydrogenation should be capable of being taken from the atmospheric gas via the reaction mixture. The hydrogen may also be produced in situ in solution from suitable hydrogen sources. Such hydrogen sources include, for example, ammonium formate, formic acid and other formates, hydrazines in the presence of metal ions such as $Fe^{2+}/Fe^{3+}$ and other hydrogen sources known from the prior art.

The reaction time for the asymmetric hydrogenation is between 2 and 8 hours to completion, preferably between 4 and 6 hours, most preferably 4 hours.

N-Benzyl-L-phenylephrine 2 is reacted to form the phenylephrine hydrochloride 3 by palladium-catalysed hydrogenating debenzylation. The reaction mixture for the asymmetric hydrogenation may be combined with a palladium catalyst without any further working up (method A).

In this method, the reaction solution for the asymmetric hydrogenation is combined with activated charcoal and a palladium chloride solution immediately after the reaction and is hydrogenated under a pressure of 1 to 5 bar, preferably 2–3 bar. Further processing is carried out using methods known from the literature.

Preferably, however, N-benzyl-L-phenylephrine 2 is first isolated from the reaction solution of the asymmetric hydrogenation by simple working up and crystallisation as a crude product and then subjected to palladium-catalysed debenzylation in solution with hydrogen under pressure (method B, cf Examples). In fact, surprisingly, it has been found that the separation of enantiomers required after asymmetric hydrogenation can be carried out more easily and successfully at the N-benzyl-L-phenylephrine stage 2 than at the L-phenylephrine or hydrochloride stage 3.

The process according to the invention will now be explained by the Examples which follow. The skilled person is aware that the Examples serve only as an illustration and should not be regarded as limiting.

EXAMPLES

Preparation of the Catalyst Solution 4.3 g of dichloro-bis-[(cycloocta- 1,5-diene)rhodium (I)] and 9.4 g of RR-MCCPM (2R,4R)-4-(dicyclohexyl-phosphino)-2-(diphenylphosphino-methyl)- N-methyl-aminocarbonylpyrrolidine are added to 2 liters of degassed methanol under protective gas and stirred for 30 min. at ambient temperature.

Asymmetric hydrogenation of N-benzyl-N-methyl-2-amino-m-hydroxyacetophenone hydrochloride 1 to form N-benzyl-L-phenylephrine 2:

80 kg of N-benzyl-N-methyl-2-amino-m-hydroxyacetophenone hydrochloride 1, 0.58 kg of triethylamine and 240 l of methanol are placed in a 500 l autoclave, degassed and combined with the above catalyst solution. Then the mixture is heated to 50–55° C. and a pressure of 20 bar is produced using hydrogen. After about 4 h total hydrogenation has taken place.

Further reaction of N-benzyl-L-phenylephrine 2 to form L-phenylephrine hydrochloride 3

Method A

The abovementioned hydrogenation solution is combined, in a second 500 l stirred vessel, with 0.8 kg of activated charcoal and about 69 g of palladium in the form of palladium chloride solution and hydrogenated at 2 bar of $H_2$ pressure. After the reaction the solvent mixture is distilled off in vacuo and about 80 l of water are added. Then a pH of about 9.5 is achieved using 50% potassium carbonate solution at about 65° C. and the solution is cooled to 10–15° C. The crystalline precipitate is separated off and washed with about 100 l of $H_2O$. The crude base is added to about 120 l of water, adjusted to a pH of about 6.5 with concentrated hydrochloric acid (about 18 l) and heated to 50–60° C. The solution is mixed with activated charcoal (2.4 kg) and filtered. Then the pH is adjusted to 2.5–3.0 and most of the water is distilled off in vacuo. The residue is dissolved in about 145 l of isopropanol. This is then evaporated down to about 100 l and cooled to 10–15° C. The L-phenylephrine hydrochloride 3 which crystallises out is separated off and freed from isopropanol by centrifuging and drying. L-phenylephrine hydrochloride 3 is obtained in a yield of about 40 kg (about 71% based on N-benzyl-N-methyl-2-amino-m-hydroxyacetophenone hydrochloride 1) and in a chemical purity of >99% and an optical purity of >96% ee.

Method B

The hydrogenation solution described above is distilled off in vacuo, mixed with 118 l of water, heated to 50–60° C. and mixed with activated charcoal. After the removal of the charcoal, about 80 l of water and 235 l of methanol are added and heated to 35–45° C. Then the solution is combined with about 57 l of concentrated ammonia solution and cooled to about 15–25° C. The crystalline precipitate formed is separated off, washed with about 100 l of water and dried. About 57 kg of N-benzyl-N-methyl-2-amino-m-hydroxyacetophenone are obtained as a free base. This is mixed with about 114 l of water, 18 l of concentrated hydrochloric acid (pH about 5.5–6.5) and about 57 g of palladium in the form of palladium-charcoal and hydrogenated at 55°–65° C. at 2 bar of $H_2$ pressure. After the reaction has ended (1–2 h) the toluene produced is distilled off azeotropically with water. Then activated charcoal is added to the solution, which is then filtered and adjusted to a pH of 3.4–3.6 before about 110 l of water are distilled off. The residue is taken up in about 150 l of isopropanol and cooled to 15–20° C. The product which crystallises out is separated off and dried. After drying, about 38 kg of L-phenylephrine hydrochloride 3 are obtained. The mother liquor is distilled off in vacuo to leave a residue which is taken up in about 20 l of water, adjusted to a pH of 6.2–6.5 with concentrated hydrochloric acid, combined with activated charcoal, filtered and finally adjusted to a pH of 3.4–3.6. Then the solvent is removed by distillation, the residue is dissolved in about 15 l of isopropanol and crystallised again. After separation and drying, about 4.5 kg of L-phenylephrine hydrochloride 3 are obtained. The total yield of 3 is about 42.5 kg (76% based on N-benzyl-N-methyl-2-amino-m-hydroxyacetophenone hydrochloride 1). The chemical purity is >99% and the optical purity is >99% ee.

What is claimed is:

1. A process for preparing L-phenylephrine hydrochloride from prochiral N-benzyl-N-methyl-2-amino-m-hydroxyacetophenone hydrochloride, the process comprising:
   (a) asymmetrically hydrogenating prochiral N-benzyl-N-methyl-2-amino-m-hydroxyacetophenone hydrochloride using a catalyst system comprising [Rh(COD)Cl]$_2$ and a chiral, bidentate phosphine ligand, to obtain N-benzyl-L-phenylephrine; and
   (b) reductively debenzylating the N-benzyl-L-phenylephrine obtained from step (a) using palladium and hydrogen, to obtain L-phenylephrine hydrochloride,
wherein the molar ration of N-benzyl-N-methyl-2-amino-m-hydroxyacetophenone hydrochloride to [Rh(COD)Cl]$_2$ is between 5000:1 and 100,000:1.

2. The process according to claim 1, wherein the chiral, bidentate phosphine ligand is (2R,4R)-4-(dicyclohexylphosphino)-2-(diphenylphosphinomethyl)-N-methylaminocarbonylpyrrolidine.

3. The process according to claim 1, wherein the chiral, bidentate phosphine ligand is polymer-bound (2R,4R)-4-(dicyclohexylphosphino)-2-(diphenylphosphinomethyl)-N-methylaminocarbonylpyrrolidine.

4. The process according to claim 1, wherein the asymmetric hydrogenation is carried out in a temperature range of from 40° C. to 100° C.

5. The process according to claim 4, wherein the asymmetric hydrogenation is carried out in a temperature range of from 40° C. to 60° C.

6. The process according to claim 5, wherein the asymmetric hydrogenation is carried out in a temperature range of from 50° C. to 55° C.

7. The process according to claim 1, wherein the asymmetric hydrogenation is carried out under a pressure of more than 1 bar up to 100 bar.

8. The process according to claim 7, wherein the asymmetric hydrogenation is carried out under a pressure of 10 bar to 50 bar.

9. The process according to claim 8, wherein the asymmetric hydrogenation is carried out under a pressure of 20 bar.

10. The process according to claim 9, wherein the asymmetric hydrogenation is carried out in a protic solvent.

11. The process according to claim 1, wherein the asymmetric hydrogenation is carried out in a branched or unbranched $C_1$–$C_8$-alkanol as the solvent.

12. The process according to claim 11, wherein the solvent is methanol, ethanol, n-propanol, and/or isopropanol.

13. The process according to claim 10, wherein the solvent for the asymmetric hydrogenation contains water.

14. The process according to claims 1–13, wherein the molar ratio of N-benzyl-N-methyl-2-amino-m-hydroxyacetophenone hydrochloride to [Rh(COD)Cl]$_2$ in the asymmetric hydrogenation is between 5,000:1 and 20,000:1.

15. The process according to claim 14, wherein the molar ratio of N-benzyl-N-methyl-2-amino-m-hydroxyacetophenone hydrochloride to [Rh(COD)Cl]$_2$ in the asymmetric hydrogenation is about 10,000:1.

16. The process according to claim 1, wherein the [Rh(COD)Cl]$_2$ for the asymmetric hydrogenation is added as a pre-prepared solution.

17. The process according to claim 1, wherein the [Rh(COD)Cl]$_2$ for the asymmetric hydrogenation is produced in situ.

18. The process according to claim 1, wherein the reaction time for the asymmetric hydrogenation is between 2 and 8 hours.

19. The process according to claim 18, wherein the reaction time for the asymmetric hydrogenation is between 4 and 6 hours.

20. The process according to claim 19, wherein the reaction time for the asymmetric hydrogenation is about 4 hours.

21. The process according to claim 1, wherein, after the conclusion of the asymmetric hydrogenation of step (a), step (b) is performed by combining the reaction solution of the asymmetric hydrogenation with activated charcoal and a palladium chloride solution without working up and the resulting solution is subjected to a pressure of about 2 bar with hydrogen.

22. The process according to claim 1, wherein after the conclusion of the asymmetric hydrogenation of step (a), the N-benzyl-L-phenylephrine obtained is isolated as a crude product and then dissolved in water at a pH in the range from about 5–7 to form an aqueous solution, and step (b) is performed by adding palladium charcoal to the aqueous solution and subjecting the resulting solution to a pressure of 1 to 5 bar with hydrogen.

* * * * *

UNITED STATES PATENT AND TRADEMARK OFFICE
CERTIFICATE OF CORRECTION

PATENT NO. : 6,187,956 B1
DATED : February 13, 2001
INVENTOR(S) : Klingler, Franz D., Wolter, Lienhard and Dietrich, Wolfgang It is certified that error appears in the above-identified patent and that said Letters Patent is hereby corrected as shown below:

Title page,
Item [12], "Klinger et al" should read -- Klingler et al --.
Item [75], Inventors, "Franz Dietrich Klinger" should read -- Franz Dietrich Klingler --.
Item [56], References Cited, under OTHER PUBLICATIONS,
"Rodium" should read -- Rhodium --.

Column 4,
Line 20, "aminocarbonylpyrrolid" should read -- aminocarbonylpyrrolidine --.

Signed and Sealed this

Twenty-third Day of July, 2002

*Attest:*

*Attesting Officer*

JAMES E. ROGAN
*Director of the United States Patent and Trademark Office*